United States Patent [19]

Gerasimov et al.

[11] 4,209,744
[45] Jun. 24, 1980

[54] EDDY CURRENT DEVICE FOR AUTOMATICALLY TESTING THE QUALITY OF ELONGATED ELECTRICALLY CONDUCTIVE OBJECTS BY NON-DESTRUCTIVE TECHNIQUES

[76] Inventors: Viktor G. Gerasimov, ulitsa Energeticheskaya, 8, korpus 1, kv. 144; Vladimir V. Kljuev, ulitsa Volgina, 13, kv. 69; Viktor B. Kuznetsov, Novogireevskaya ulitsa, 14, korpus 2, kv. 29; Viktor P. Kurozaev, ulitsa Bobruiskaya, 6, kv. 29; Viktor I. Rogachev, Jurievsky pereulok, 22, korpus 2, kv. 55; Vasily V. Sukhorukov, ulitsa 2 Vladimirskaya, 50, korpus 2, kv. 51; Jury M. Ulitin, Beskudnikovsky bulvar, 27, korpus 2, kv. 55; Jury K. Fedosenko, ulitsa Chugunnye vorota, 3, korpus 1, kv. 39, all of Moscow, U.S.S.R.

[21] Appl. No.: 889,931

[22] Filed: Mar. 27, 1978

Related U.S. Application Data

[63] Continuation-in-part of Ser. No. 681,489, Apr. 29, 1976, abandoned.

[51] Int. Cl.² .............................................. G01R 33/00
[52] U.S. Cl. .................................... 324/241; 324/240
[58] Field of Search ............... 324/217, 226, 227, 228, 324/240, 241

[56] References Cited

U.S. PATENT DOCUMENTS

| | | | |
|---|---|---|---|
| 2,300,999 | 11/1942 | Williams | 324/226 |
| 3,056,681 | 9/1962 | Hochschild | 324/238 |
| 3,343,079 | 9/1967 | Cronch | 324/227 |
| 3,394,303 | 7/1968 | Cressman et al. | 324/225 |
| 3,528,003 | 9/1970 | Forster | 324/227 |
| 3,538,433 | 11/1970 | Wood et al. | 324/227 |
| 3,895,290 | 7/1975 | Audenard et al. | 324/233 |

OTHER PUBLICATIONS

Gunkel, W. A., A Method for Defect Discrimination etc., Material Eval., Feb. 1964, pp. 80–85.
Stumm, W., New Development In E. C. Testing etc., Material Eval., Jul. 1971, pp. 141–147.

*Primary Examiner*—Rudolph V. Rolinec
*Assistant Examiner*—Walter E. Snow
*Attorney, Agent, or Firm*—Lackenbach, Lilling & Siegel

[57] ABSTRACT

An automatic eddy current inspection system for discrimination of defects in elongated parts made of conducting materials comprises an alternating current generator connected in series to an amplitude selector via a differential encircling eddy-current transducer and a detector. The amplitude selector has two selection levels. The system also comprises a signal analyzer with a controllable switch and the following counters: a counter for determining the length of long cracks; a minor defects counter; a major defects counter; and a counter for determining the length of tested parts. The outputs of the counters are connected to the inputs of a sorter having its outputs connected to quality grade indicators. The controllable switch of the signal analyzer has its control input connected to the output of the amplitude selector which corresponds to a higher selection level. The input of the counter for determining the length of long cracks is connected to the output of a long cracks detecting circuit which has three inputs. The first input of said circuit is connected to a "part length-code" transducer, while its second and third inputs are connected to the inputs of the amplitude selector. The input of the minor defects counter and the input of the major defects counter are connected to respective outputs of an inhibitor which has three inputs connected as follows: the first one is connected in series to the control circuit of the controllable switch of the signal analyzer; the second one is connected to the output of the amplitude selector which corresponds to a higher selection level; and the third one, control, is connected to the output of the long cracks detecting unit. The input of the counter for determining the length of tested parts is connected to the output of the "part length-code" transducer.

2 Claims, 26 Drawing Figures

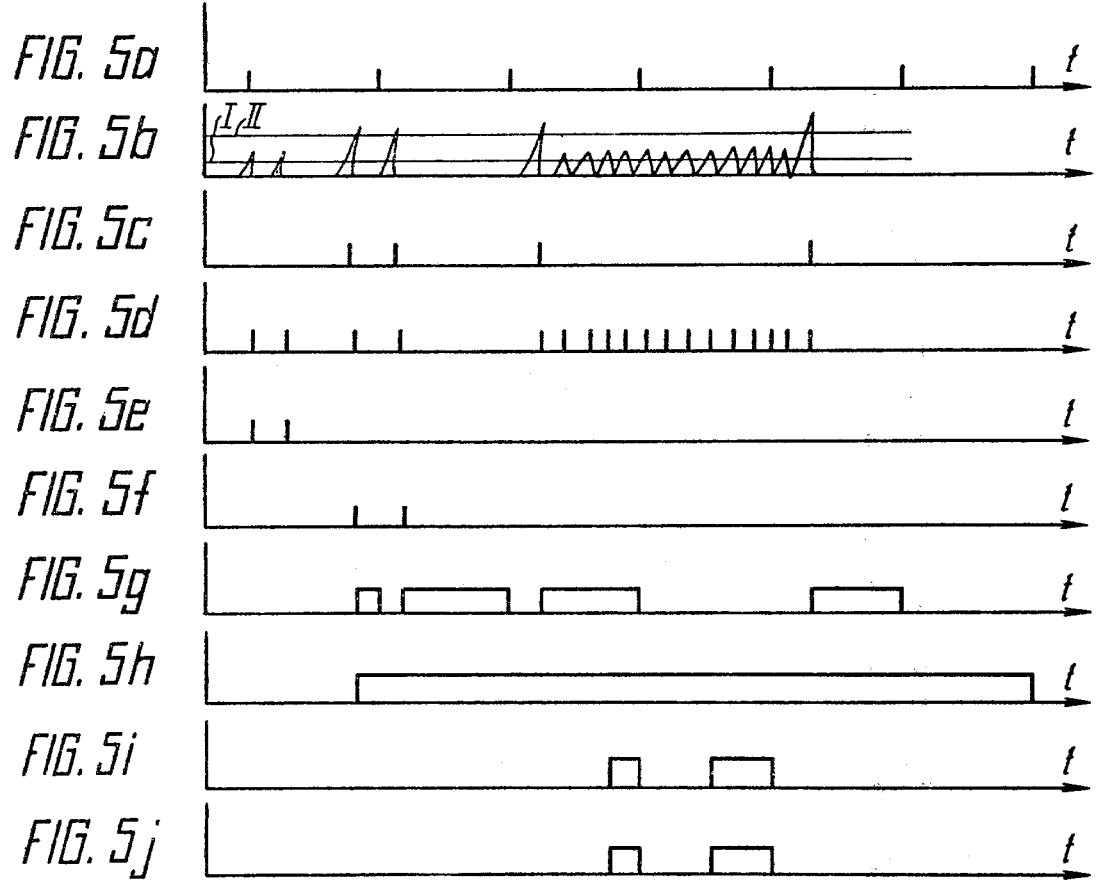

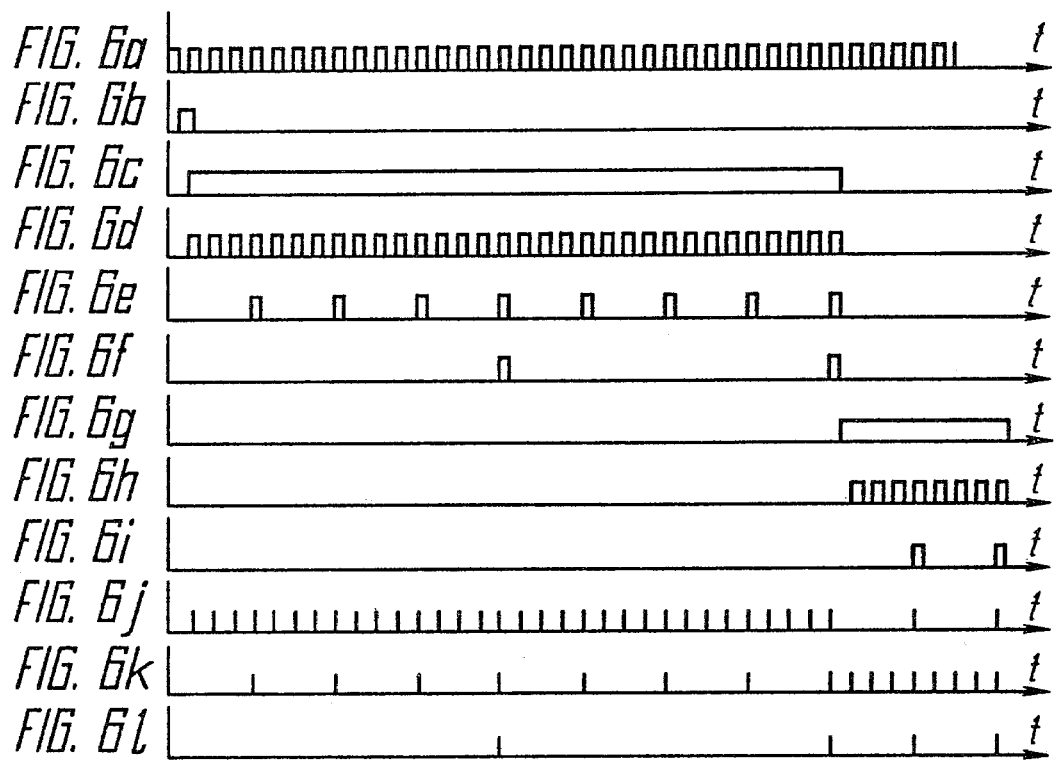

EDDY CURRENT DEVICE FOR AUTOMATICALLY TESTING THE QUALITY OF ELONGATED ELECTRICALLY CONDUCTIVE OBJECTS BY NON-DESTRUCTIVE TECHNIQUES

REFERENCES TO CO-PENDING APPLICATIONS

The present application is a continuation-in-part of our co-pending application Ser. No. 681,489 "A Device for Nondestructive Testing of Elongated Parts Made of Conducting Materials" filed on Apr. 29, 1976, now abandon.

FIELD OF THE INVENTION

The present invention relates to nondestructive techniques and in particular to an automatic eddy current inspection system for detecting defects in elongated parts made of discrimination conducting materials.

The invention can find application in metallurgy, rolling production, machine building, nuclear technology, vacuum tube production and electronic engineering to automatically check the quality of rolled parts, wires, rods and similar items made of metals, alloys or graphite.

DESCRIPTION OF THE PRIOR ART

The testing of parts and semi-finished products, such as wires of refractory metals used in vacuum tube production is of major importance in raising the efficiency of production. If such defects as cracks, flows, burrs or long cracks in a wire are detected in time, then considerable losses will be avoided in the course of production of expensive items, for instance, colour kinescopes or power oscillator tubes. These testing procedures make it also possible to increase the reliability and service life of the devices.

Various methods of nondestructive testing are used to inspect elongated parts, for instance, a wire, made of conducting materials; ultrasonic, optical, magnetic, thermal. There is also an eddy-current method. A drawback of the ultrasonic method consists in that it requires that there be an acoustic contact with the test sample. Usually the contact is established through a liquid, which makes the control equipment rather sophisticated. The optical method does not allow for the discrimination of subsurface defects and yields low authenticity when parts with contaminated surfaces are tested. The magnetic method can be employed only when test samples are made of ferromagnetic materials. The thermal (infra-red) method requires that the test samples be heated and does not allow longitudinal defects to be discriminated.

The method that is most widely used at present for the testing of elongated parts of conducting materials employs the principle of eddy currents. Its advantage with respect to the above methods consists in that it allows for the testing of the quality of elongated parts at a high rate and remotely, i.e., in a noncontact manner, while the parts may be made of conducting materials both ferromagnetic and nonferromagnetic and may have contaminated surfaces (for instance, covered with a graphite grease) or varnish-paint coatings.

Known in the art is a device for nondestructive testing of wires with the use of the eddy-current method, called "Defectoterm 2.186" and manufactured by F. Ferster Institute (Federal Republic of Germany).

This device comprises a high-frequency alternating current generator whose output is connected to a differential encircling eddy-current transducer through which a test wire is passed. The differential encircling eddy-current transducer comprises one or more exciting and sensing windings. An alternating current flowing through the exciting windings induces eddy currents in the test wire. The intensity of the eddy currents is affected by defects such as cracks, spill defects or burrs in the wire.

The sensing windings are arranged coaxially with respect to the exciting windings and to the test wire. Since the sensing windings are spaced from one another and are connected in series opposition, the transducer output voltage is determined by the difference in properties between individual sections of the test wire which are located opposite to respective sensing windings. The latter are connected, via a detector, to an amplitude selector having at least two selection levels.

The described device also comprises a signal analyzer having three counters as follows: a major defects counter, a minor defects counter and a counter for determining the length of tested parts, which is connected to a "part length-code" transducer.

One output of the detector corresponding to the lower selection level is connected to the input of the minor defects counter of the signal analyzer. Another output of the amplitude selector corresponding to the higher selection level is connected to the input of the major defects counter.

The output of the detector is connected to the signal input of an oscilloscope. The "part length-code" transducer designed to produce pulse signals at time intervals corresponding to the preset length of a section of the test wire is connected to the signal analyzer.

With known devices, parts, for instance, wire, are sorted into grades after testing either manually by an operator or automatically by a computer in accordance with numerical data that describe several quality parameters such as the length of defective sections and the number of major and minor defects. The difference between major and minor defects is based on the depth of the latter.

The known devices suffer from low testing rate and require an operator. In the case when a computer is included in the system, the latter becomes exceedingly complex and expensive.

The signal analyzer of the above device when used to test elongated parts does not detect the most dangerous defects of the latter, i.e., the defects in the form of long cracks. This is due to the fact that it comprises counters which only determine the quantities of major and minor defects of short size. Therefore, it can detect only minor and major defects of short size.

Moreover, the devices described above do not determine accurately enough the position of a defective section along the test part because the oscilloscope is not synchronized to the movement of the part during the test. The position of a defective section of the part should be determined accurately in case it is required, for instance, to set the boundaries of sorting.

The known devices also suffer from the low authenticity of the test results. This is due to the fact that the sensitivity of any of these devices depends on the level of the eddy-current transducer unbalance. The unbalance level may fluctuate under the effect of destabilizing factors in the course of operation. Self-test circuits built in the known devices simulate signals at the outputs thereof which are applied either only to the input of the detector or only to the eddy-current transducer. Hence, the operability of the device as a whole cannot be checked.

SUMMARY OF THE INVENTION

An object of the present invention is to increase the rate of testing of elongated parts made of conducting materials.

Another object of the present invention is to simplify the design and operation of the device.

Still another of the present invention is to increase the authenticity of test results.

And still another object of the present invention is to increase the accuracy with which the position of a defective section is determined in the test part.

These objects are achieved by means of an automatic eddy current inspection system for discrimination of defects in elongated parts made of conducting materials comprising: an alternating current generator whose output is connected to a differential encircling eddy-current transducer through which an elongated part of a conducting material passes during testing which comprises two sensing windings connected in series opposition and coupled inductively to its exciting winding and which has its output connected, via a detector, to an amplitude selector having at least two selection levels and two outputs connected to a signal analyzer; a "part length-code" transducer whose output is connected to the signal analyzer; and an oscilloscope having one synchronization input and at least two signal inputs, one of which is connected to the output of the detector. According to the invention, the signal analyzer comprises: a counter for determining the length of long cracks, a minor defects counter and a major defects counter; a sorter, the inputs of which are connected to the outputs of said counters: a quality grade indicator unit connected to the output of the sorter; a counter for determining the length of tested parts, the input of which is connected to the output of the "part length-code" transducer and the output of which is coupled to the input of the sorter; a long cracks detecting circuit having two inputs connected to the outputs of the amplitude selector, a third input connected to the "part length-code" transducer and an output connected to the input of the counter for determining the length of long cracks; an inhibitor having two inputs, one of which is connected to the output of the amplitude selector corresponding to the higher selection level and a control input connected to the long cracks detecting circuit, and having two outputs, the input of the minor defects counter being connected to one of said outputs of the inhibitor and the input of the major defects counter being connected to the second output of said inhibitor; and a controllable switch having a control input connected to the output of the amplitude selector corresponding to the higher selection level, the second input of the inhibitor being connected in series with the cotrol circuit of said controllable switch.

Advantageously, the proposed system comprises testing means and a switching unit having an input connected to the output of the testing means that serves to simulate signals from the "part length-code" transducer and having two control inputs, one of which control inputs is connected to the output of the testing means that serves to simulate signals from the differential encircling eddy-current transducer characteristic of minor defects and the second one of said control inputs is connected to the output of the testing means that serves to simulate signals from the differential encircling eddy-current transducer characteristic of major defects, the switching unit being provided with two controllable switches, a first switch and a first resistor being inserted in series with the control circuit of one of said two controllable switches and a second switch and a second resistor being inserted in series with the control circuit of the second controllable switch, the resistance of the second resistor differs from that of the first resistor, the leads of said control circuits being connected in pairs so that one pair is grounded and another one is coupled to the connection point of the sensing windings of the differential encircling eddy-current transducer, said switching unit being also provided with a third switch having one lead connected to the "part length-code" transducer and the other lead that serves as said input of said switching unit, and the control inputs of the controllable switches being used as the control inputs of the switching unit.

The advantages of the system described above with respect to those known in the art are as follows.

The new system has a higher rate of control since it ensures a completely automatic sorting procedure for test parts in accordance with several quality grades. The quality grades correspond to the combinations of the number and length of sections having defects of different types. These combinations are preset during the sorter adjustment procedure.

The length of sections with long cracks is evaluated by the respective counter connected to the output of the long cracks detecting circuit. A long crack is detected by the number of lower level signals per unit of length of the test part which follow the higher level signals.

While having a higher, with respect to known devices, rate of control, the above system requires no computer, which makes the inspection system much simpler. The functions of determining quality grades in the system are performed by a sorter which carries out a minimum number of simple logical operations.

Another advantage of the above system, when compared with those known in the prior art, is that it determines the position of the defective section of the test part much more accurately. This is achieved by means of synchronizing the oscilloscope sweep rate with the speed of the test part and by means of producing a marker scale on the oscilloscope screen, the markers corresponding to the preset length of a section of the test part. Signals from the "part length-code" transducer, the time intervals between the signals corresponding to the preset length of the part's section, are fed to the synchronization input of the sweep oscillator of the oscilloscope via a frequency divider. The same signals are applied to one of the signal inputs of the oscilloscope while the second signal input of the latter is fed with signals from the detector output. Due to this arrangement the oscilloscope displays an oscillogram with a scale of markers placed at intervals that correspond to the length of a section of the test part preset by the "part length-code" transducer and independent of the speed with which the part moves. Using the marker scale, it is possible to determine the position of the defective section of the test part quite accurately.

The third advantage of the above system in comparison with those known in the prior art is that it provides a higher degree of test result authenticity, which is ensured due to the availability of the testing means which simulates signals characteristic of defects of the test part and feeds them simultaneously to the differential encircling eddy-current transducer and to the signal analyzer. Signals from the testing means are passed to the eddy-current transducer via the switching unit whose output is coupled to one of the sensing windings of that transducer. The signals arranged in combinations corresponding to long cracks, and to major and minor defects of short size cause the unbalance of the eddy-current transducer in the case when a resistor of a higher or lower resistance is connected in parallel with one of the sensing windings of the eddy-current transducer via the controllable switches of the switching unit. As a result, the detector output generates signals corresponding to higher and lower level signals of the amplitude selector. At the same time, the testing means feeds the output of the "part length-code" transducer with signals simulating those generated by the "part length-code" transducer. Thus, the signal analyzer and the oscilloscope are fed with signals similar to those that appear in the system when defective sections of the test part pass through the eddy-current transducer and the output indicators display the quality grades of the part preset by the testing means with the result that the operability of the whole system can be tested.

DESCRIPTION OF THE DRAWINGS

These and other objects and advantages of the present invention will become apparent from the following description of its embodiments given by way of example and taken together with the accompanying drawings in which:

FIG. 3 is an oscillogram of signals displayed on the oscilloscope screen, according to the invention;

FIGS. 5 $a, b, c, d, e, f, g, h, i, j$ show time diagrams of signals as they appear at the outputs of the "part length-code" transducer, the detector, the amplitude selector, the inhibitor, the flip-flops of the long cracks detecting circuit and the AND gate which serves as the output of the long cracks detecting circuit, according to the invention;

FIGS. 6 $a, b, c, d, e, f, g, h, i, j, k, l$ show time diagrams of signals as they appear at the outputs of an oscillator, a push-button, flip-flops, AND gates, frequency dividers, timing pulse shapers and signals of the testing means that correspond to those generated by the differential encircling eddy-current transducer in response to minor and major defects, according to the invention.

DESCRIPTION OF THE INVENTION

Figure 1:
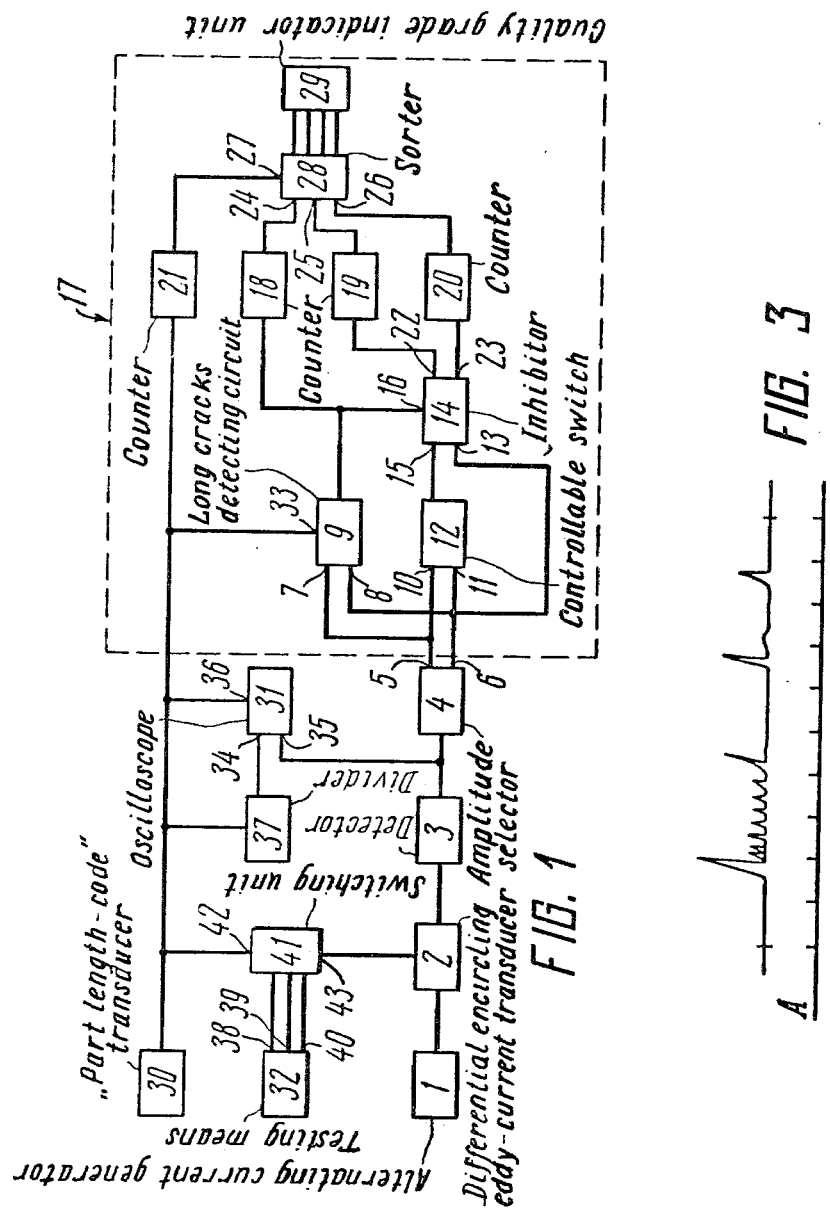
FIG. 1 is a block diagram of an automatic eddy current system for discrimination of defects in elongated parts made of conducting materials, according to the invention.

The automatic eddy current inspection system for discrimination of defects in elongated parts made of conducting materials comprises, according to the invention, an alternating current generator 1 (FIG. 1) whose output is connected to a differential encircling eddy-current transducer 2. The eddy-current transducer 2 comprises one or more exciting windings 2a (FIG. 2) and sensing windings 2b, 2c. An alternating current flows through the exciting windings 2a to induce eddy currents in the test part made of conducting material, for instance, in a wire of a refractory metal. The intensity of these eddy currents depends on the presence of defects in the test wire, such as cracks, spill defects or burrs. The sensing windings 2b, 2c are arranged coaxially with respect to the exciting windings 2a and the test wire. Since the sensing windings 2b, 2c are spaced from one another and are connected in series opposition, the output voltage of the eddy-current transducer 2 is determined by the difference in properties between individual sections of the test wire which are located opposite to respective sensing windings.

The sensing windings 2b, 2c are connected, via a detector 3, to an amplitude selector 4 (FIG. 1) having at least two selection levels which correspond to its two outputs 5,6.

The detector 3 and the amplitude selector 4 are of known design.

The outputs 5,6 of the amplitude selector 4 are connected, respectively, to inputs 7,8 of a long cracks detecting circuit 9. The output 6 which corresponds to the higher selection level is connected to an input 13 of an inhibitor 14. The output 5 which corresponds to the lower selection level is connected, via a controllable switch 12, to an input 15 of the inhibitor 14. A control input 16 of the inhibitor 14 is connected to the output of the long cracks detecting circuit 9.

The long cracks detecting circuit 9, the controllable switch 12 and the inhibitor 14 are incorporated in a signal analyzer 17.

The signal analyzer 17 also comprises a counter 18 for determining the length of long cracks, a minor defects counter 19, a major defects counter 20 and a counter 21 for determining the length of tested parts. The input of the counter 18 is connected to the output of the long cracks detecting circuit 9. The input of the counter 19 is connected to an output 22 of the inhibitor 14. The input of the counter 20 is connected to an output 23 of the inhibitor 14. The outputs of the counters 18, 19, 20, 21 are connected, respectively, to inputs 24, 25, 26, 27 of a sorter 28 which discriminates between test parts in accordance with preset quality grades. The outputs of the sorter 28 are connected to the inputs of a quality grade indicator unit 29. Due to the availability of the signal analyzer 17 described above, the system can automatically sort out the test parts in accordance with several quality grades depending on the presence of major and minor defects and long cracks in them. This arrangement makes it possible to increase the rate of control and to simplify the control system.

In addition to units 1, 2, 3, 4, 9, 12, 14, 18, 19, 20, 21, 28, 29, the system also comprises a "part length-code" transducer 30, an oscilloscope 31 and testing means 32. The transducer 30 is connected to an input 33 of the long cracks detecting circuit 9 and to the input of the counter 21 for determining the length of tested parts. The oscilloscope 31 has a synchronization input 34 and signal inputs 35, 36. The synchronization input 34 is connected to the output of the transducer 30 via a frequency divider 37. The signal input 35 is connected to the output of the detector 3, while the signal input 36 is coupled to the transducer 30. The screen of the oscilloscope 31 displays a marker scale A (FIG. 3), the intervals between the markers corresponding to the preset length of a section of the test part.

Due to the described above synchronization between the sweep rate of the oscilloscope 31 (FIG. 1) and the speed of the test part as well as due to the marker scale A (FIG. 3) displayed on the screen of the oscilloscope 31, the intervals between the markers corresponding to the preset length of a section of the test part, a defective section of the test part, for instance, a wire, is determined with a high degree of precision. This is clearly illustrated in FIG. 3 wherein an oscillogram of respective signals is shown.

The testing means 32 (FIG. 1) included in the system has three outputs 38, 39, 40 connected to the inputs of a switching unit 41. The output 38, that serves to simulate signals from the "part length-code" transducer 30, is connected to the input of the switching unit 41. The outputs 39, 40, that serve to simulate signals from the eddy-current transducer 2 characteristic of minor and major defects, respectively, are connected to respective control inputs of the switching unit 41. An output 42 of the switching unit 41 is connected to the transducer 30, while an output 43 of the switching unit 41 is connected to the connection point of the sensing windings 2b, 2c (FIG. 2) of the eddy-current transducer 2.

Another embodiment includes the switching unit 41 having its output connected to the lead of the mid point of the exciting winding 2a of the eddy-current transducer 2.

The use of testing means 32 which checks the system as a whole ensures a higher degree of authenticity of results obtained in the course of testing of elongated parts made of conducting materials.

Figure 4:
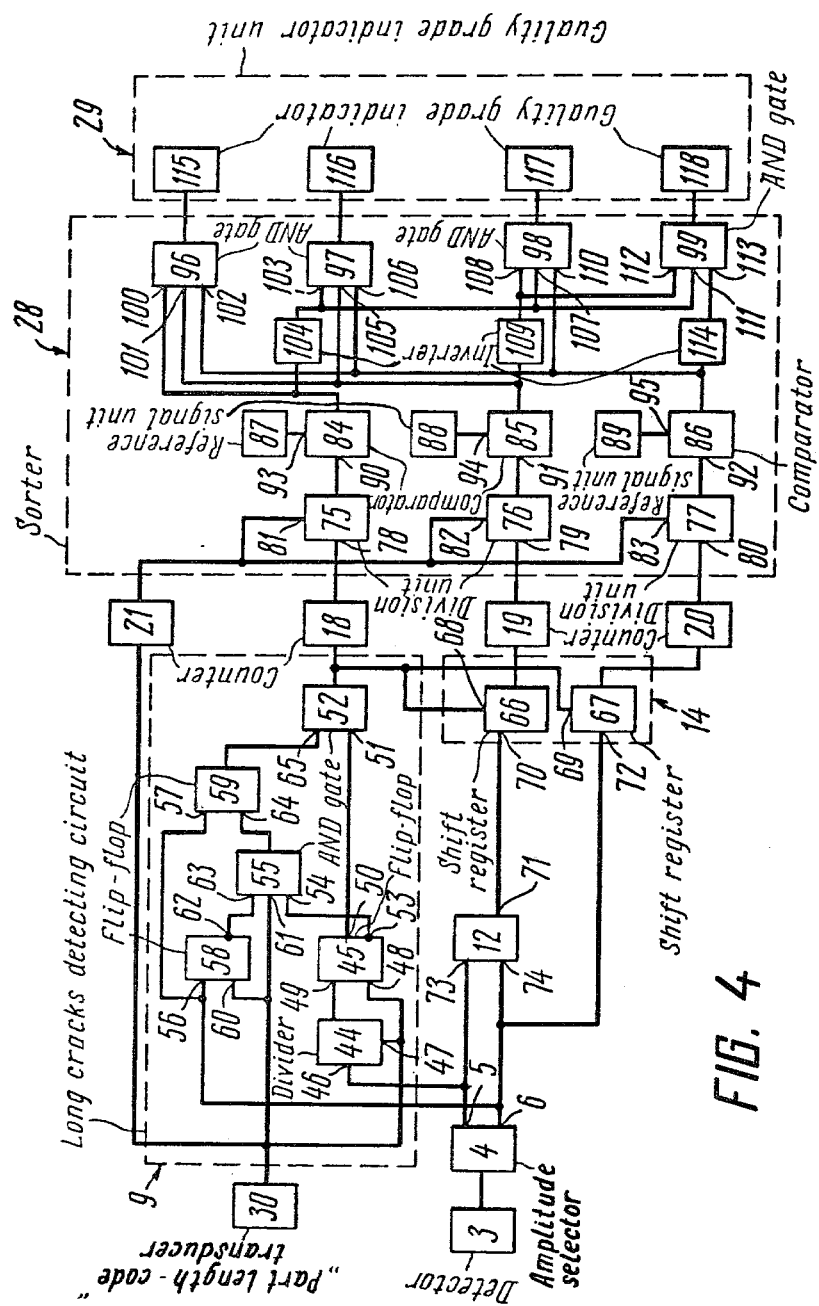
FIG. 4 is a block diagram of the signal analyzer, according to the invention.

The long cracks detecting circuit 9 (FIG. 1) may be implemented as a scale-of-4 frequency divider 44 (FIG. 4) and a flip-flop 45. A complementing input of the frequency divider 44 is connected to the output 5 of the amplitude selector 4 which corresponds to the lower selection level. As reset input 47 of the frequency divider 44 and a reset input 48 of the flip-flop 45 are connected to the output of the transducer 30 the design of which is well known. A set input 49 of the flip-flop 45 is connected to the output of the frequency divider 44. An output 50 of the flip-flop 45 is connected to an input 51 of an AND gate 52 of a known design.

An inverse output 53 of the flip-flop 45 is connected to an input 54 of an AND gate 55.

The output 6 of the amplitude selector 4 which corresponds to the higher selection level is connected to a set input 56 of a flip-flop 58 and to a set input 57 of a flip-flop 59.

The output of the transducer 30 is connected to a reset input 60 of the flip-flop 58 and to an input 61 of the AND gate 55. An inverse output 62 of the flip-flop 58 is connected to an input 63 of the AND gate 55.

The output of the AND gate 55 is connected to a reset input 64 of the flip-flop 59.

The output of the flip-flop 59 is connected to an input 65 of the AND gate 52. The counter 18 for determining the length of long cracks is connected to the output of the AND gate 52.

The inhibitor 14 (FIG. 1) comprises two shift registers 66, 67 (FIG. 4) of known design.

The shift register 67 is a one-bit circuit and the shift register 66 is a four-bit circuit. The shift registers 66, 67 have their respective reset inputs 68, 69 connected to the output of the AND gate 52. A write and shift input 70 of the shift register 66 is connected to an output 71 of the controllable switch 12 (FIG. 1) of known design.

A write and shift input 72 of the shift register 67 is connected to the output 6 of the amplitude selector 4 which corresponds to the higher selection level.

An input 73 of the controllable switch 12 is coupled to the output 5 of the amplitude selector 4 which corresponds to the lower selection level.

A control input 74 of the controllable switch 12 is connected to the output 6 of the amplitude selector 4 which corresponds to the higher selection level. If no signal is present on the control input 74, the controllable switch 12 is closed.

The sorter 28 comprises division units 75, 76, 77 of known design.

A dividend input 78 of the division unit 75 is connected to the output of the counter 18 for determining the length of long cracks. A dividend input 79 of the division unit 76 is connected to the output of the minor defects counter 19. A dividend input 80 of the division unit 77 is connected to the major defects counter 20. Divisor inputs 81, 82, 83 of the division units 75, 76, 77, respectively, are connected to the output of the counter 21 for determining the length of tested parts.

The sorter 28 also comprises comparators 84, 85, 86 and reference signal units 87, 88, 89. Inputs 90, 91, 92 of the comparators 84, 85, 86 are connected to the outputs of the division units 75, 76, 77. Inputs 93, 94, 95 of the comparators 84, 85, 86 are connected to the reference signal units 87, 88, 89.

The comparators 84, 85, 86 and the reference signal units 87, 88, 89 are of known design.

The sorter 28 also comprises AND gates 96, 97, 98, 99. Inputs 100, 101, 102 of the AND gate 96 are coupled to the outputs of the comparators 84, 85, 86, respectively. An input 103 of the AND gate 97 is connected, via an inverter 104, to the output of the comparator 84. Inputs 105, 106 of the AND gate 97 are connected to the outputs of the comparators 85, 86, respectively. Inputs 107, 108 of the AND gate 98 are connected, via inverters 104, 109, to the outputs of the comparators 84, 85, respectively. An input 110 of the AND gate 98 is connected to the output of the comparator 86. Inputs 111, 112, 113 of the AND gate 99 are connected, via inverters 104, 109, 114, to the outputs of the comparators 84, 85, 86, respectively. The inverters 104, 109, 114 are of known design.

The outputs of the AND gates 96, 97, 98, 99 are connected, respectively, to quality grade indicators 115, 116, 117, 118 of the quality grade indicator unit 29. The quality grade indicators 115, 116, 117, 118 serve to display the lowest, the medium, the first and the highest grades of test parts, respectively.

The testing means 32 incorporates an oscillator 119 (FIG. 2) and a flip-flop 120. A set input 121 of the flip-flop 120 is connected to a TEST push-button 122. The output of the oscillator 119 is coupled to an input 123 of the AND gate 124 having its input 125 connected to the output of the flip-flop 120.

Connected to the output of the AND gate 124 is a scale-of-4 frequency divider 126 which is connected in series to a scale-of-4 frequency divider 127, to a complementing flip-flop 128 and to a flip-flop 129. The output of the flip-flop 129 is connected to an input 130 of an AND gate 131 whose input 132 is connected to the output of the oscillator 119.

The output of the complementing flip-flop 128 is connected to a reset input 133 of the flip-flop 120.

The output of the AND gate 131 is connected to the input of a scale-of-4 frequency divider 134 and to an input 135 of an OR gate 136.

Figure 2:
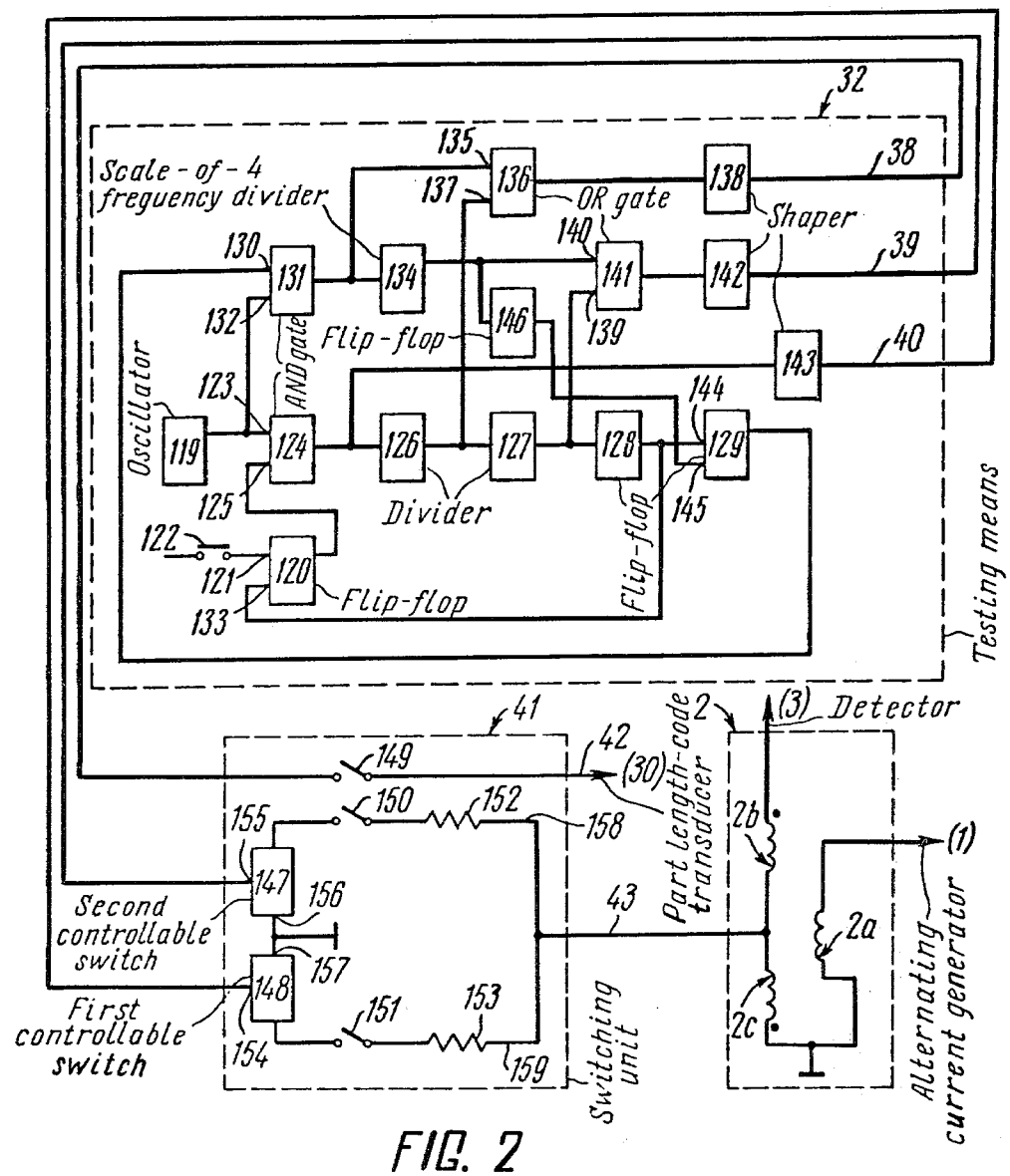
FIG. 2 shows a block diagram of the testing means and its connections to the differential encircling eddy-current transducer, according to the invention.

An input 137 of the OR gate 136 is connected to the output of the frequency divider 126 and the output of the OR gate 136 is connected to a timing pulse shaper 138 of the "part length-code" transducer 30 (FIG. 1). An output 38 of the timing pulse shaper 138 (FIG. 2) is connected to the input of the switching unit 41.

The outputs of the scale-of-4 frequency dividers 127, 134 are coupled to inputs 139, 140 of an OR gate 141, respectively.

The output of the OR gate 141 is connected to a shaper 142 of high signals which correspond to signals generated by the differential eddy-current transducer 2 in case of major defects. An output 39 of the shaper 142 (FIG. 2) is connected to the second control input of the switching unit 41.

The output of the AND gate 124 is connected to a shaper 143 of low signals generated by the transducer 2 in case of minor defects. An output 40 of the shaper 143 is connected to the first control input of the switching unit 41.

A set input 144 of the flip-flop 129 is coupled to the output of the flip-flop 128 and a reset input 145 of the flip-flop 129 is coupled to the output of a flip-flop 146 having its input connected to the output of the frequency divider 134.

The switching unit 41 comprises controllable switches 147, 148, switches 149, 150, 151 and resistors 152, 153. The first control input 154 of the switching unit 41 serves as the control input of the first controllable switch 148 and is connected to the output 40 of the shaper 143. The second control input 155 of the switching unit 41 serves as the control input of the second controllable switch 147 and is connected to the output 39 of the shaper 142.

The first switch 149 (FIG. 2) is placed between the input of the switching unit 41, connected to the output 38 of the shaper 138, and the first output 42 of the switching unit 41, connected to the "part length-code" transducer 30 (FIG. 1). The second switch 151 is connected in series with the resistor 153 to the control circuit of the first controllable switch 148, while the third switch 150 is connected in series with the resistor 152 to the control circuit of the second controllable switch 147. The value of the resistor 152 is less than that of the resistor 153. Control circuit leads 156 and 157, 158 and 159 of the controllable switches 147, 148 are connected in pairs so that the lead pair 156, 157 is grounded and the lead pair 158, 159 constitutes the second output 43 of the switching unit 41, connected to the common point of the sensing windings 2b, 2c of the eddy-current transducer 2. The exciting winding 2a of the eddy-current transducer 2 has one its lead connected to ground and the other lead connected to the output of the alternating current generator 1. The lead of the sensing winding 2b is connected to the nonsymmetrical input of the detector 3, whereas the lead of the sensing winding 2c is grounded.

The proposed system uses a number of known circuits, such as the detector 3 (FIG. 1) of the amplitude selector 4, the scale-of-4 frequency dividers 37, 44, 126, 127, 134, the shift registers 66, 67, the counters 18, 19, 20, 21, the "parth length-code" transducer 30, the oscilloscope 31, the flip-flops 45,58,59,120,128,129, the AND gates 52,55,96,97,98,99,124,131, the OR gates 136,141, the controllable switch 12, the division units 84,85,86, the comparators 84,85,86 and the reference signal units 87, 88,89 which are illustrated, for instance, in "The Modern Encyclopedia of Automated Processes and Industrial Electronics", Moscow, 1962; respective pages concerned with the items described are as follows: p. 311, vol. 1. p. 62, vol. 1; p. 305, vol. 1; p. 191, vol. 3; p. 454, vol. 3; p. 64, vol. 3; p. 457, vol. 2; p. 103, vol. 4; p. 207, vol. 4; p. 207, vol. 2; p. 44; vol. 2; p. 96, vol. 1; p. 402, vol. 3.

The operation of the system is illustrated with the help of time diagrams (FIGS. 5a, b, c, d, e, f, g, h, i, j) which depict the shapes of signal trains at the outputs of various circuits as follows: FIG. 5a shows a signal at the output of the "part length-code" transducer 30; FIG. 5b shows a signal at the output of the detector 3; FIG. 5c shows a signal at the output 6 of the amplitude selector 4 which corresponds to the higher selection level; FIG. 5d shows a signal at the output 5 of the amplitude selector 4 which corresponds to the lower selection level; FIG. 5e shows a signal at the output of the shift register 66; FIG. 5f shows a signal at the output of the shift register 67; FIG. 5g shows a signal at the output of the flip-flop 58; FIG. 5h shows a signal at the output of the flip-flop 59; FIG. 5i shows a signal at the output 50 of the flip-flop 45; FIG. 5j shows a signal at the output of the AND gate 52.

The X-axis of the time diagrams shows time t and the Y-axis in all figures, except 5b, logical levels at the outputs of respective circuits. The higher level corresponds to the presence of a signal or to a condition under which it can pass, while the lower level corresponds to the absence of a signal or to a condition under which it cannot pass.

The Y-axis in FIG. 5b shows voltage values. Lines I and II correspond to the voltages at two selection levels, the lower and the higher, of the amplitude selector 4.

The operation of the testing means 32 is illustrated with the help of time diagrams (FIGS. 6a,b,c,d,e,f,g,h, i,j,k,l) which depict the shape of signal trains at the outputs of the following circuits: FIG. 6a shows a signal at the output of the oscillator 119; FIG. 6b shows a signal obtained from the push-button 122; FIG. 6c shows a signal at the output of the flip-flop 120; FIG. 6d shows a signal at the output of the AND gate 124; FIG. 6e shows a signal at the output of the frequency divider 126; FIG. 6f shows a signal at the output of the frequency divider 127; FIG. 6g shows a signal at the output of the flip-flop 129; FIG. 6h shows a signal at the output of the AND gate 131; FIG. 6i shows a signal at the output of the frequency divider 134; FIG. 6j shows a signal at the output of the low signal shaper 143; FIG. 6k shows a signal at the output of the timing pulse shaper 138; FIG. 6l shows a signal at the output of the high signal shaper 142.

The X-axis of the time diagrams shows time t and the Y-axis, the logical levels at the outputs of respective circuits. The higher level corresponds to the presence of a signal or to a condition under which it can pass, while the lower level corresponds to the absence of a signal or to a condition under which it cannot pass.

The automatic eddy current inspection system for discrimination of defects in parts made of conducting materials operates as follows.

The a.c. generator 1 (FIG. 1) produces an alternating magnetic field in the differential encircling eddy-current transducer 2. Induced in the test part which is within the eddy-current transducer 2 are eddy currents, the distribution of which depends on the properties of the test part and also on the defects that it might have. As the terminals of the sensing windings 2b,2c (FIG. 2) of the transducer 2, connected in series opposition, there appears an alternating voltage, the magnitude of which is determined by the difference between the properties of the sections of the test part that correspond to the positions of the sensing coils. The passage of the part through the eddy-current transducer 2 modulates the high-frequency voltage across the sensing windings in accordance with the variations of the part's properties along its length. When a section of the part with a long crack passes through the eddy-current transducer 2, the detector 3 will produce a higher level electrical signal (FIG. 5b) followed by at least four lower level signals. When there is a section of the part having a short in length and deep-seated defect, such as a burr or a cavern passing through the transducer 2 (FIG. 1), the detector 3 will produce one higher level signal (FIG. 5b). Minor defects, such as scratches or notches will produce lower level signals at the output of the detector 3 (FIG. 5b). The amplitude selector 4 has two selection levels: the higher one II and the lower one I (FIG. 5b). When signals as shown in FIG. 5b arrive at the input of the amplitude selector 4 (FIG. 1), the output 6 of the latter which corresponds to the higher selection level will produce signals as shown in FIG. 5c, while the output 5 (FIG. 1) of the amplitude selector 4 which corresponds to the lower selection level will produce signal as shown in FIG. 5d.

The movement of the test part through the transducer 2 (FIG. 1) will cause the "part length-code" transducer 30 to start operating and to produce time signals (FIG. 5a) which will appear at its output, for instance, after every 0.1 m of the length of the test part. From the output of the "part length-code" transducer 30 (FIG. 4) the signals will arrive to the counter 21 for determining the length of tested parts and to the reset inputs 47, 48 of the divider 44 and the flip-flop 45.

The signal appearing at the reset inputs 47, 48 will cause the divider 44 to operate and to be reset to the 0 state, i.e., to the state which corresponds to the absence of data in its registers.

The flip-flop 45 is also transferred to the off position. Signals from the output of the transducer 30 will also arrive at the input 61 of the AND gate 55 and to the reset input 60 of the flip-flop 58 causing the latter to operate. The inputs 54 and 63 of the AND gate 55 will receive signals from the inverse outputs of the flip-flops 45, 58 which prevent the signal from being passed from the input 61 of the AND gate 55 to its output. The result is that the reset input 64 of the flip-flop 59 will receive a signal from the output of the AND gate 55 which will trigger it off.

When the input of the amplitude selector 4 receives a signal from the output of the detector 3 which corresponds to a long crack and which is shown in FIG. 5b, the output 6 of the amplitude selector 4 corresponding to the higher selection level will produce a signal that will correspond in time to the signal as shown in FIG. 5c. The output 5 of the selector 4 corresponding to the lower selection level will produce signals as shown in FIG. 5d. The signal from the output 6 is applied to the set inputs 56, 57 of the flip-flops 58, 59, respectively, causing them to operate and to produce signals as shown in FIG. 5g, 5h, respectively. The signal from the output 6 is applied to the input 72 of the shift register 67 and is stored there.

The signals from the output 5 as shown in FIG. 5d arrive, via the controllable switch 12, at the input 70 of the shift register 66 and are stored in its locations in succession.

The signals from the output 5 also arrive to the input 46 of the scale-of-4 frequency divider 44. When the input 46 receives four signals belonging to a signal train as shown in FIG. 5d, the divider 44 will operate and produce a signal to be fed to the set input 49 of the flip-flop 45. The flip-flop 45 will operate to produce, at its output 50, a signal shown in FIG. 5i which corresponds in time to the fourth signal as shown in FIG. 5d. The inputs 51, 65 of the AND gate 52 receive signals from the output 50 of the flip-flop 45 and from the output of the flip-flop 59. These signals cause the AND gate 52 to open and to produce a signal which is applied to the reset inputs 68, 69 of the shift registers 66, 67, respectively, to drive them to the 0 state and to preclude the subsequent storage of data in them.

The next time signal from the "part length-code" transducer 30 as shown in FIG. 5a is applied to the input 61 of the AND gate 55 and to the reset inputs 47,48,60, of the divider 44 and the flip-flops 45,58, respectively. The signals appearing at the inverse input 53 of the flip-flop 45 and at the inverse input of the flip-flop 58 are applied to the inputs 54,63 of the AND gate 55 to prevent the pulse from the input 61 from passing to the output of that gate. The flip-flop 59 remains in its initial state. The input 51 of the AND gate 52 is fed with a signal arriving from the output 50 of the flip-flop 45 and prevents a signal appearing at the input 65 of the AND gate 52 from the output of the flip-flop 59 from passing to the output of that gate.

The result is that the AND gate 52 is driven to cut off. At this moment the counter 18 for determining the length of long cracks will be notified that the test part has a long crack.

During the following time interval between the time signals as generated by the "part length-code" transducer 30 and shown in FIG. 5a, the output 5 of the amplitude selector 4 will produce signals as shown in FIG. 5d which will arrive, via the controllable switch 12, to the input 70 of the shift register 66 and are stored as its digits. When the input 46 receives four subsequent signals, the divider 44 will operate and at its output there will appear a signal fed to the set input 49 of the flip-flop 45. The latter will operate to produce a signal that will appear at its output 50 (see FIG. 5i).

The inputs 51, 65 of the AND gate 52 will receive signals from the outputs of flip-flops 45, 59 which will cause the AND gate 52 to open. The signal appearing at the output of the AND gate 52 will arrive at the reset inputs 68,69 of the shift registers 66,67, respectively, driving them to the 0 state and preventing the locations of the shift register 66 from storing any subsequent data. The next time signal from the "part length-code" transducer 30 as shown in FIG. 5a arrives at the reset inputs 47, 48 of the divider 44 and the flip-flop 45, respectively. The input 61 of the AND gate 55 receives a signal from the transducer 30, while the input 54 of the AND gate 55 receives a signal from the inverse output 53 of the flip-flop 45 which prevents the signal from the input 61 from passing to the output of the AND gate 55. As a result, the flip-flop 59 remains in its initial state.

Since the trigger 45 has operated under the effect of a signal applied to its set input 49, the divider 44 takes up the 0 state. The result is that the input 51 of the AND gate 52 receives a signal from the output 50 of the flip-flop 45 which prevents the signal from the input 65 from passing to the output of the AND gate 52. At the same time the counter 18 will be notified that the test part has a long crack.

During the last time interval corresponding to the section of the test part that has a long crack and lying between time signals of the transducer 30, the number of signals arriving from the output 5 of the amplitude selector 4, via the controllable switch 12, to the input 70 of the shift register 66 and to the input 46 of the divider 44 will be less than four. Hence, these signals will not cause the divider 44 and the flip-flop 45 to operate until their reset inputs 47, 48 receive the next time pulse from the transducer 30. This signal will cause the divider 44 to operate with the result that the latter takes up the 0 state. At the same time, the signal from the transducer 30 arrives at the input 61 of the AND gate 55. The inputs 54,63 of the AND gate 55 receive signals from the inverse outputs of the flip-flops 45,58, respectively, which prevent the signal from the input 61 from passing to the output of the AND gate 55. Now, the flip-flop 59 will operate.

When the input of the amplitude selector 4 receives lower level signals from the output of the detector 3 as shown in FIG. 5b which indicate that there is a section of the test part with minor defects passing through the eddy-current transducer 2, the output 5 of the amplitude selector 4 will produce signals in a due time succession (see FIG. 5d). These signals arrive at the input 73 of the controllable switch 12 whose output will cause signals to be stored in the locations of the shift register 66. When the four digits of the register 66 are occupied, the arrival of a fifth signal at its input will cause the shift register 66 to operate. Its output will produce a signal and the counter 19 will be notified that the test part has minor defects.

Simultaneously signals from the output 5 of the amplitude selector 4 also arrive at the set input 46 of the divider 44. If the number of signals that arrive during the time interval between two time signals are produced by the "part length-code" transducer 30 exceeds three, the divider 44 will operate and produce a signal at its output. This signal will vause the flip-flop 45 to operate and to produce, at its input 50, a signal which is fed to the input 51 of the AND gate 52. However, the AND gate 52 will not open in this case since its input 65 receives a signal from the output of the flip-flop 59 which prevents the signal from the input 51 of the AND gate 52 from passing to its output.

When the input of the amplitude selector 4 receives higher level signals arriving from the output of the detector 3 as shown in FIG. 5b which indicate that there is a section of the test part having major defects passing through the eddy-current transducer 2, the outputs 5,6 of the amplitude selector 4 will produce signals shown in FIGS. 5c,5d, respectively. These signals are applied to the inputs 73,74, respectively, of the controllable switch 12, while the signal from the output 6 is also fed to the input 72 of the shift register 67. Here the controllable switch 12 will break the circuit, thus preventing the signals from its input 74 from passing to the input 70 of the shift register 66. Signals from the output 6 of the amplitude selector 4 arrive at the input 72 of the shift register 67. The latter will operate and the counter 20 will be notified that the test part has short-sized major defects.

The signals from the output 6 of the amplitude selector 4 also arrive at the set inputs 56,57, respectively, of the flip-flops 58,59. The signals from the output 5 arrive at the set input 46 of the divider 44. The flip-flops 58,59 will operate. The divider 44 and the flip-flop 45 will not operate since the number of signals arriving at the input 46 of the divider 44 from the output 5 of the amplitude selector 4 within the time interval between two time signals as generated by the "part length-code" transducer 30 is small (less than four).

When the test part with sections having various defects passes through the differential encircling eddy-current transducer 2 (FIG. 1), the signals appearing in this case at the output of the detector 3 will pass to the signal input 35 of the oscilloscope 31. The second signal input 36 and the synchronization input 34 of the oscilloscope 31 will receive, via the frequency divider 37, time signals produced by the "part length-code" transducer 30. Thus, the screen of the oscilloscope 31 will display oscillograms of signals carrying information on the presence of various defects in the test part (see FIG. 2).

Due to the fact that the sweep rate of the oscilloscope 31 (FIG. 1) is locked in time to the movement of the test part and that the screen of the oscilloscope 31 displays the scale A (FIG. 3) with markers which correspond to the preset length of sections of the test part, it become possible to visually monitor the presence of a defect and to accurately determine its position in the test part.

Signals from the outputs of the counters 18 (FIG. 1), 19 and 20 arrive at the dividend inputs 78, 79, 80 of the division units 75,76,77, respectively. The divisor inputs 81, 82, 83 of the division units 75,76, 77, respectively, receive a signal from the counter 21 which corresponds to the length of the tested part, for instance, wire. The quotient signals from the outputs of the division units 75,76,77 arrive at the inputs 90,91,92 of respective comparators 84,85,86. The other inputs 93,94,95 of the comparators are fed with signals from respective reference signal units 87,88,89. If the signals arriving at the inputs 90,91,92 of respective comparators 84,85,86 exceed those arriving from the reference signal units 87,88,89, the comparators will operate to produce signals at their outputs. These signals pass from the outputs of the comparators 84,85,86 to respective inputs 100,101,102 of the AND gate 96. The latter will operate and produce a signal at its output. The output signal of the AND gate 96 activates the lowest quality grade indicator 115. The AND gates 97,98,99 in this case will not operate.

The AND gate 97 will not operate since its input 103 has received, via the inverter 104, a signal from the output of the comparator 84 which prevents the gate from opening. The AND gate 98 will not operate since its inputs 107,108 receive, via the inverters 104, 109, signals from the comparators 84,85 which prevent the gate from opening. The AND gate 99 will not operate since its inputs 111,112, 113 receive, via the inverters 104,109,114, signals from the outputs of the comparators 84,85,86 which prevent the gate from opening.

If the signals arriving at the inputs 91,92 of the comparators 85,86, respectively, exceed those which are passed to the inputs 94,95 of the comparators from the reference signal units 88, 89 and a signal which arrives at the input 90 of the comparator 84 does not exceed that which is present on the input 93 of the comparator 84, the outputs of the comparators 85,86 will have signals and the output of the comparators 84 will have no signal. The signals from the outputs of the comparators 85,86 arrive at the inputs 105,106 of the AND gate 97.

The third input 103 of the AND gate 97 also receives a signal after the output signal of the comparator 84 has been inverted by the inverter 104. The AND gate 97 will operate and its output signal activates the medium quality grade indicator 116. The AND gates 96, 98, 99 will not operate due to the reasons specified above.

If the relationship between the signals arriving at the inputs 90 and 93, 91 and 94, 92 and 95 of respective comparators 84,85,86 is such that no signals are present on the outputs of the comparators 84,85, but a signal is present on the output of the comparator 86, the inputs 107,108 of the AND gate 98 will receive signals from respective comparators 84,85 via the inverters 104, 109. The input 110 of the AND gate 98 receives a signal directly from the output of the comparator 86. The AND gate 98 will operate and its output signal activates the first quality grade indicator 117. The AND gates 96,97,99 will not operate in this case.

If the relationship between the signals arriving at the inputs 90 and 93, 91 and 94, 92 and 95 of respective comparators 84,85,86 is such that no signals are present on the outputs of the comparators 84,85,86, the inputs 111,112, 113 of the AND gate 99 receive signals, via the inverters 104,109,114, which cause the gate to operate. The output of the AND gate 99 produces a signal which activates the highest quality grade indicator 118. The AND gates 96,97,98 will not operate in this case.

The testing means 32 and the switching unit 41 (FIG. 2) of the system operate as follows.

The oscillator 119 produces a series of square-wave signals as shown in FIG. 6a. When the testing means 32 is activated, the input 121 of the flip-flop 120 will receive a signal from the push-button 122 as shown in FIG. 6b. This signal causes the flip-flop 120 to operate. A signal appearing at the output of the flip-flop 120 (see FIG. 6c) arrives at the input 125 of the AND gate 124. The other input 123 of the AND gate 124 receives signals from the oscillator 119. The AND gate 124 will operate and its output produces signals as shown in FIG. 6d. These signals pass to the shaper 143 producing low signals characteristic of minor defects of the test part and to the input of the scale-of-4 frequency divider 126. Every fourth signal from the output of the AND gate 124 arrives, via the divider 126, to the input 137 of the OR gate 136 and then to the shaper 138 of time signals shown in FIG. 6k. Every sixteenth signal from the output of the AND gate 124 arrives, via the dividers 126, 127 and via the OR gate 141, at the shaper 142 of the high signals characteristic of major defects of the part (see FIG. 6l). When there are thirty two signals from the output of the AND gate 124, the dividers 126, 127 operate and the flip-flop 128 takes up the 0 state. A signal from the output of the flip-flop 128 is applied concurrently to the input 144 of the flip-flop 129 and to the input 133 of the flip-flop 120 so as to activate them.

The input 125 of the AND gate 124 receives from the output of the flip-flop 120 a signal which prevents the signal obtained from the oscillator 119 from passing to the output of the AND gate 124 from the input 123 of the latter. Therefore, the oscillator 119 appears to be disconnected from both the divider 126 and the shaper 143. No signals are delivered from the output of the AND gate 124 to the divider 126 and the shaper 143 of small signals. A signal from the output of the flip-flop 129 (as shown in FIG. 6g) arrives at the input 130 of the AND gate 131, while the input 132 of the gate receives a signal from the oscillator 119. The AND gate 131 will operate and its output produces signals as shown in FIG. 6h. The signals from the output of the AND gate 131 arrives at the input of the divider 134 and to the input 135 of the OR gate 136. Now, signals can pass to the output of the OR gate 136 and to the time signal shaper 138.

Every fourth signal arriving from the output of the AND gate 131 (see FIG. 6h) causes the divider 134 to operate and to produce signals at its output (see FIG. 6i). These signals are fed to the input 140 of the OR gate 141. The latter will operate and its output signals pass to the high signal shaper 142.

When there are eight signals (see FIG. 6h) arriving from the output of the gate 131, the divider 134 will operate and produces a signal which from its output will arrive, via the flip-flop 146, to the reset input 145 of the flip-flop 129 to cause the latter to operate. The output of the flip-flop 129 produces a signal which arrives at the input 130 of the AND gate 131 and prevents the signal from the input 132 from passing to the output of the AND gate 132. Therefore, the oscillator 119 is disconnected from the divider 131 of the OR gate 136.

The signals from the output 38 of the shaper 138 (as shown in FIG. 6k) arrive, via the closed switch 149 of the switching unit 149, at the first output 42 of the switching unit 41 and serve to modulate the signals from the "part length-code" transducer 30 (FIG. 1).

The signals from the output 40 of the shaper 143 (as shown in FIG. 6j) arrive at the first control input 154 of the switching unit 41 with the result that the first controllable switch 148 (FIG. 2) is closed. The resistor 153 of a high resistance is connected, via the closed second switch 151 and via the closed control circuit of the first controllable switch 148, in parallel with the sensing winding 2c of the differential encircling eddy-current transducer 2. This causes the unbalance of the latter which corresponds to lower selection level signals of the amplitude selector 4.

The signals from the output of the eddy-current transducer 2 arrive at the input of the detector 3.

The signals from the output 39 of the shaper 142 (as shown in FIG. 6l) arrive at the second control input 155 of the switching unit 41 with the result that the second controllable switch 147 is closed. The resistor 152 of a low resistance is connected, via the closed second switch 150 and via the closed control circuit of the second controllable switch 147, in parallel with the sensing winding 3c of the differential encircling eddy-current transducer 2. This causes the unbalance of the latter which corresponds to higher selection level signals of the amplitude selector 4. The signals from the output of the eddy-current transducer 2 arrive at the input of the detector 3.

The switches 149,150,151 of the switching unit 41 serve to disconnect the testing means 32 and are closed only when the operability of the system is to be tested.

The above-described actions constitute a cycle for testing the operability of the system, performed with the help of the testing means 32 and the switching unit 41.

During the operation of the testing means 32 and the switching unit 41, the first sixteen signals obtained in closing the first controllable switch 148 simulate minor defects of the test part. The next sixteen signals obtained in closing the first controllable switch 148 plus two signals obtained in closing the second controllable switch 147 simulate a section of the part having a crack approximately 0.4 m in length. The last two signals that appear when the second controllable switch 147 is closed simulate short-sized defects. The signals from the shaper 138 simulate time pulses of the "part length-code" transducer 30.

One test cycle therefore allows the system counters to accumulate pulses as follows: sixteen pulses in the minor defects counter 19; four pulses corresponding to a length of 0.4 m in the counter 18 for determining the length of long cracks; three pulses in the major defects counter 20; and sixteen pulses in the counter 21 for determining the length of tested parts.

The division units 75,76,77 are used to divide the numbers stored in the counters 18,19,20, respectively, by the number contained in the counter 21 for determining the length of tested parts. Signals from the outputs of the division units 75,76,77 are applied to their respective inputs 90, 91, 92 of the comparators 84,85,86. If numbers 0.02, 0.9, 0.18 are set, for instance, in the reference signal units 87,88,89, then signals appear at the outputs of the comparators 84,85,86. These signals come to respective inputs 100, 101, 102 of the AND gate 96 and activate the latter as well as the lowest quality grade indicator 115. If the latter is on, this acknowledges that the sorter 28 and the system as a whole operate properly.

The testing means 32 of the proposed system provides in a considerable increase in the authenticity of test results.

What is claimed is:

1. An automatic eddy current inspection system for discrimination of defects in elongated parts made of conducting materials, comprising an alternating current generator provided with an output, a differential encircling eddy current transducer having an output and arranged to receive an elongated part of a conducting material to be tested and being connected to said output of said alternating current generator, said differential encircling eddy-current transducer having an exciting winding connected to said output of said alternating current generator and two sensing windings connected in series opposition and coupled inductively to said exciting winding, said two sensing windings being used as said output of said differential encircling eddy-current transducer; a detector provided with an input connected to said output of said differential encircling eddy-current transducer; an amplitude selector having at least two selection levels, a plurality of outputs whose number is equal to that of said selection levels and an input connected to said output of said detector; a signal analyzer connected to said amplitude selector; a long cracks detecting circuit of said signal analyzer, provided with two inputs connected to said outputs of said amplitude selector, a third input, and an output; a "part length-code" transducer provided with an output connected to said third input of said long cracks detecting circuit; an oscilloscope having a synchronization input and at least two alarm signal inputs, one of which is electrically connected to said output of said detector, while the other alarm signal input of the oscilloscope is directly connected to said "part length-code" transducer, and said synchronization input is also connected to said "part length-code" transducer; a controllable switch of said signal analyzer having its control input connected to said output of said amplitude selector which corresponds to the higher selection level; an inhibitor of said signal analyzer provided with two inputs, one of which is connected in series to the control circuit of said controllable switch and the second one of said two inputs is connected to said output of said amplitude selector which corresponds to the higher selection level, a control input connected to said output of said long cracks detecting circuit, and two outputs; a minor defects counter of said signal analyzer, provided with an input, connected with said first output of said inhibitor, and an output; a major defects counter of said signal analyzer, provided with an input, connected to said second output of said inhibitor, and an output; a counter for determining the length of long cracks of said signal analyzer provided with an input, connected to said output of said long cracks detecting circuit, and an output; a counter for determining the length of the tested parts of said signal analyzer provided with an input, connected to said output of said "part length-code" transducer, and an output; a sorter of said signal analyzer, provided with four inputs and a plurality of outputs, one input being connected to said output of said counter for determining the length of tested parts, a second input being connected to said output of said counter for determining the length of long cracks, a third input being connected to said output of said minor defects counter, and a fourth input being connected to said output of said major defects counter; and a quality grade indicator unit having a plurality of inputs, each of which is connected to a respective output of said sorter.

2. A system as claimed in claim 1, further comprising: testing means connected to said "part length-code" transducer and to said differential encircling eddy-current transducer and having a first output used for simulating signals from said differential encircling eddy-current transducer characteristic of major detects; a second output used for simulating signals from said differential encircling eddy-current transducer characteristic of minor defects;

a third output used for simulating signals from said "part length-code" transducer, a switching unit having an input connected to said third output of said testing means, a first control input connected to said second output of said testing means, a second control input connected to said first output of said testing means, and two outputs; two controllable switches of said switching unit being provided with control inputs that serve as said control inputs of said switching unit each having two leads, one of the leads of each of the two controllable switches being grounded, three switches of said switching unit for connecting the system operation testing unit when it is required to test the system operation, one of said switches being connected between said control input and said first output of said switching unit, the second switch connected in series to a first controllable circuit of the first controllable switch, a first resistor of said first controllable circuit being connected in series to a second controllable switch, a third switch connected in series to a second controllable circuit of said second controllable switch, a second resistor of said second controllable circuit having a resistance less than the resistance of said first resistor and being connected in series to said third switch, said controllable circuits each having one lead connected to said second output of said switching unit, and the other lead connected to the ungrounded lead of said respective controllable switch, said first output of said switching unit being connected to said output of said "part length-code" transducer, and said second output of said switching unit being connected to said differential encircling eddy-current transducer.

* * * * *